(12) United States Patent
Hayashi

(10) Patent No.: US 7,338,102 B2
(45) Date of Patent: Mar. 4, 2008

(54) MANIPULATOR

(75) Inventor: Tadashi Hayashi, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 192 days.

(21) Appl. No.: 10/812,878

(22) Filed: Mar. 31, 2004

(65) Prior Publication Data

US 2004/0195851 A1 Oct. 7, 2004

(30) Foreign Application Priority Data

Apr. 4, 2003 (JP) ............................. 2003-102200

(51) Int. Cl.
*B25J 7/00* (2006.01)
*B25J 15/06* (2006.01)

(52) U.S. Cl. .................... 294/64.1; 294/64.3; 406/88

(58) Field of Classification Search ............... 294/64.1, 294/64.2, 64.3, 1.1, 65; 198/493; 406/876, 406/92, 86–88; 271/97, 98; 977/858, 872, 977/962; 414/936
See application file for complete search history.

(56) References Cited

U.S. PATENT DOCUMENTS

| | | | | |
|---|---|---|---|---|
| 2,805,898 A | * | 9/1957 | Willis, Jr. ...................... | 406/88 |
| 4,284,370 A | * | 8/1981 | Danler et al. .................. | 406/86 |
| 4,474,397 A | * | 10/1984 | Hassan et al. .............. | 294/64.3 |
| 4,865,491 A | * | 9/1989 | Sakurai ........................ | 406/87 |
| 5,125,706 A | * | 6/1992 | Kuwaki et al. ............... | 294/65 |
| 5,634,636 A | * | 6/1997 | Jackson et al. ............. | 271/225 |
| 6,062,241 A | * | 5/2000 | Tateyama et al. ............ | 134/137 |
| 6,315,342 B1 | * | 11/2001 | Torvinen .................... | 294/64.3 |
| 6,447,217 B1 | * | 9/2002 | Toda et al. ................... | 406/88 |
| 6,494,646 B1 | * | 12/2002 | Sala ............................. | 406/88 |
| 6,893,069 B1 | * | 5/2005 | Graham ..................... | 294/64.1 |
| 2004/0041422 A1 | * | 3/2004 | Nakamura ................... | 294/65 |

FOREIGN PATENT DOCUMENTS

| | | | |
|---|---|---|---|
| JP | 61-95740 | | 6/1985 |
| JP | 363222680 A | * | 9/1988 |
| JP | 4041187 A | * | 2/1992 |
| JP | 4-341438 | | 11/1992 |
| JP | 6-90770 | | 4/1994 |
| JP | 8-290377 | | 11/1996 |
| JP | 9-134946 | | 5/1997 |
| JP | 9-201783 | | 8/1997 |

(Continued)

OTHER PUBLICATIONS

U.S. Appl. No. 10/802,819, filed Mar. 18, 2004, Ichiro Okumura et al.

(Continued)

*Primary Examiner*—Dean J Kramer
(74) *Attorney, Agent, or Firm*—Fitzpatrick, Cella, Harper & Scinto

(57) ABSTRACT

This invention provides a manipulator having an arrangement which easily makes it possible to execute fine work such as attitude control while properly grasping even a minute target object. The manipulator of this invention has, at, e.g., the contact portion to a manipulation target object, an opening communicating with a pressure chamber whose pressure is controlled by a fluid control unit, and manipulates the target object by causing the fluid control unit to control inflow/outflow of a fluid through the opening.

2 Claims, 19 Drawing Sheets

FOREIGN PATENT DOCUMENTS

| | | | |
|---|---|---|---|
| JP | 2000010016 A | * | 1/2000 |
| JP | 2000-43269 | | 2/2000 |
| JP | 2000232873 A | * | 8/2000 |
| JP | 2002-257511 | * | 9/2002 |
| JP | 2002-307356 | * | 10/2002 |
| JP | 2004-16036 | * | 1/2004 |

OTHER PUBLICATIONS

U.S. Appl. No. 10/799,595, filed Mar. 15, 2004, Ichiro Okumura et al.

U.S. Appl. No. 10/815,652, filed Apr. 2, 2004, Tadashi Hayashi.

* cited by examiner

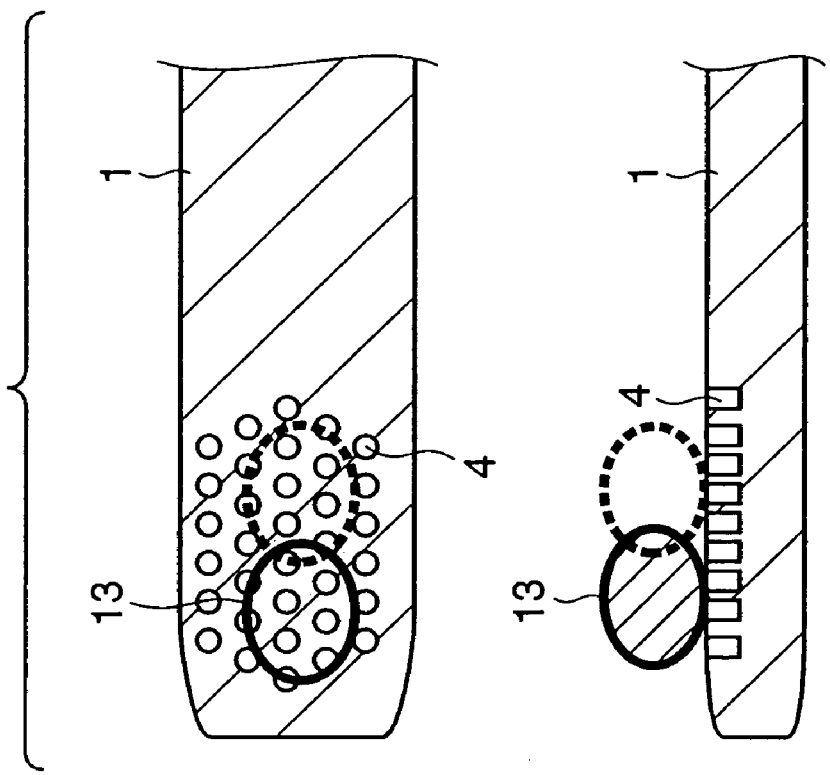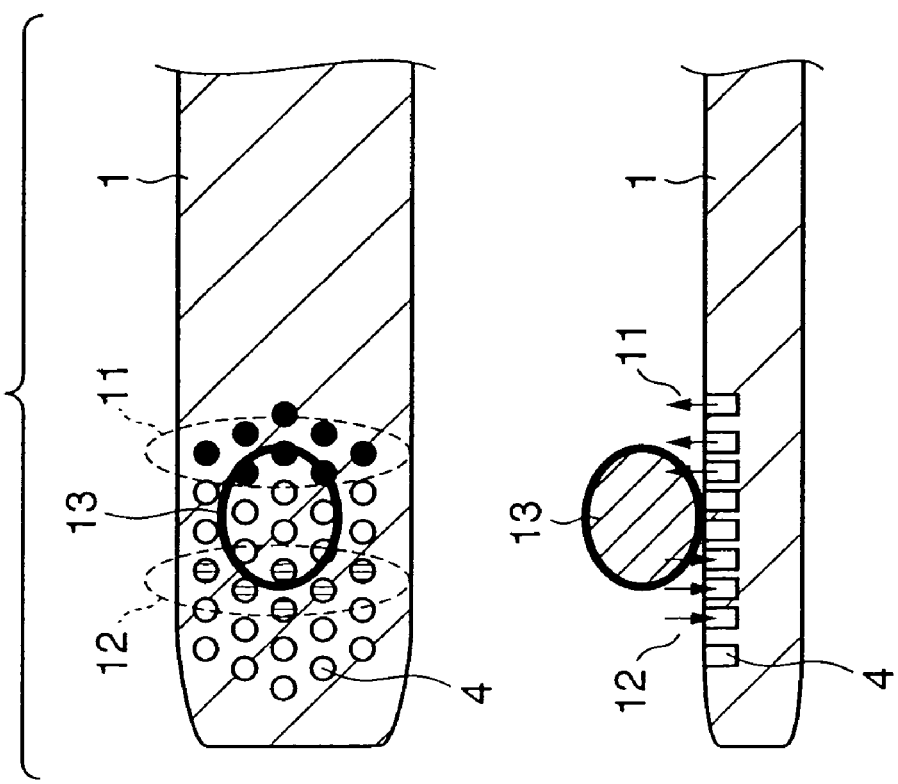

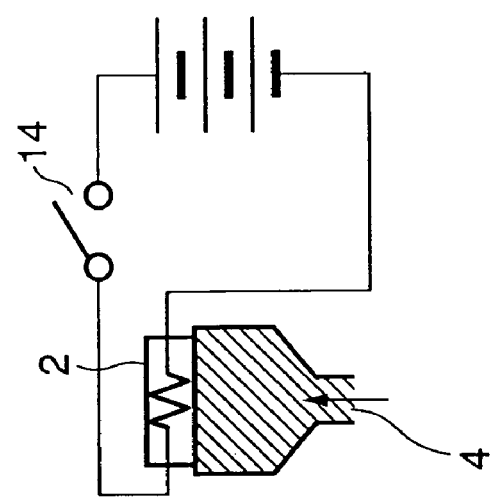
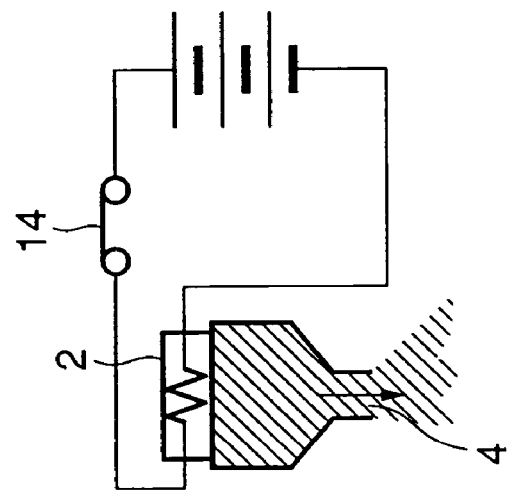
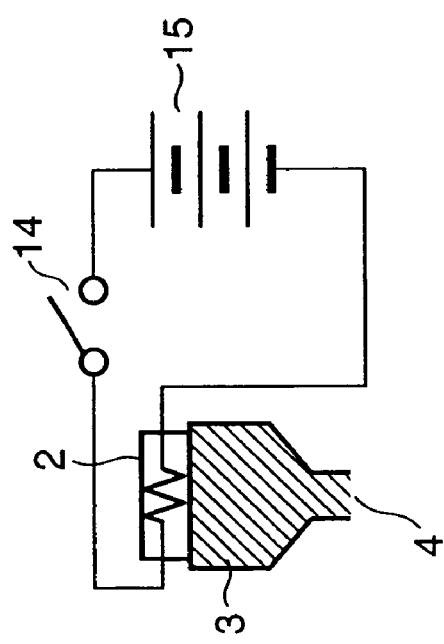

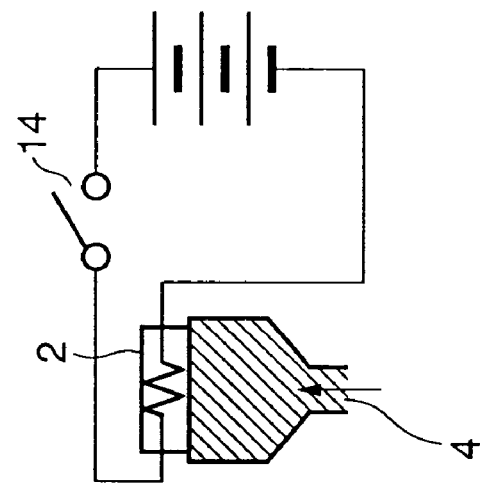
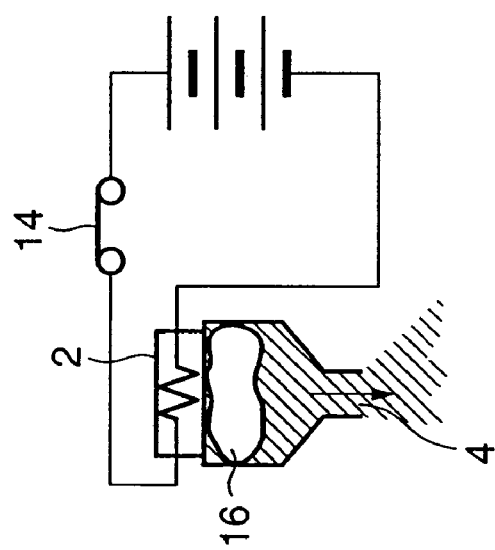
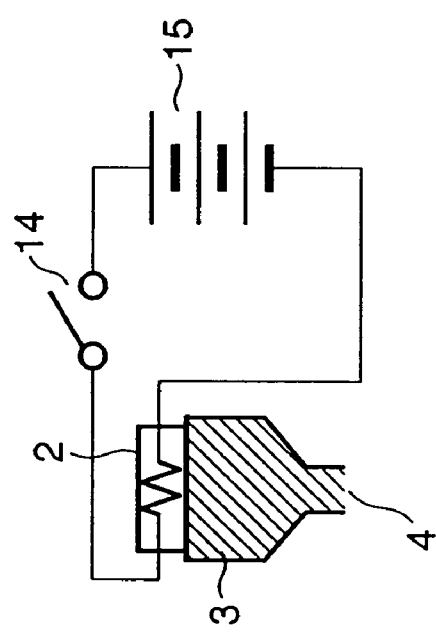

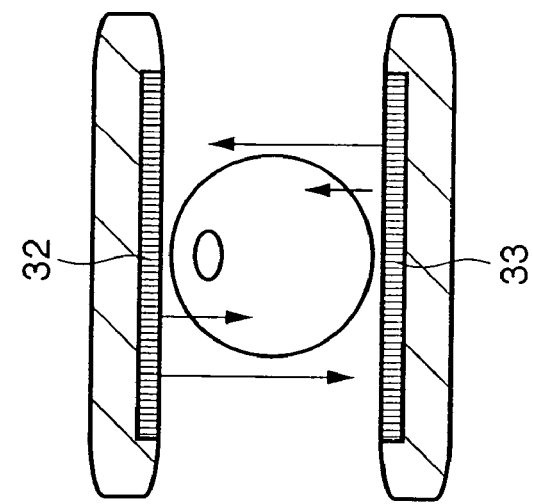
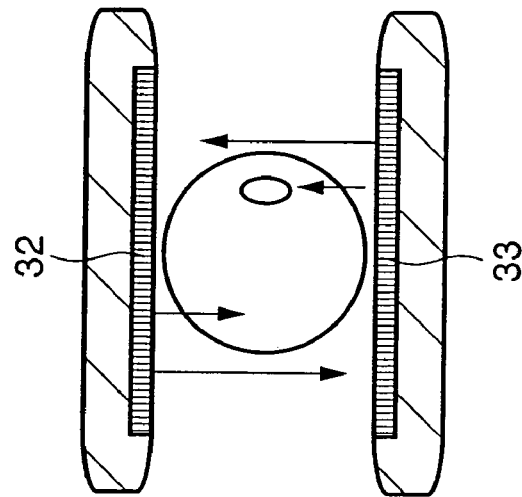
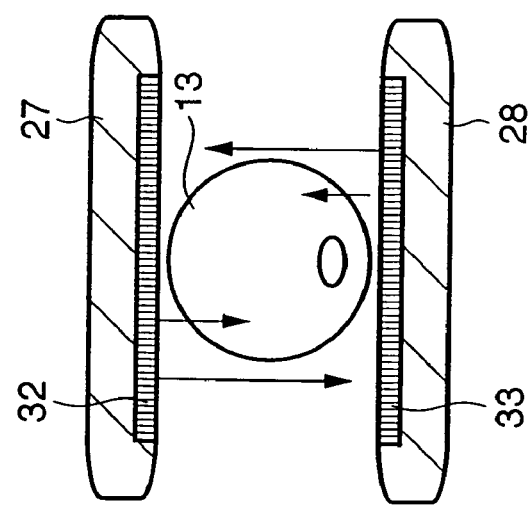

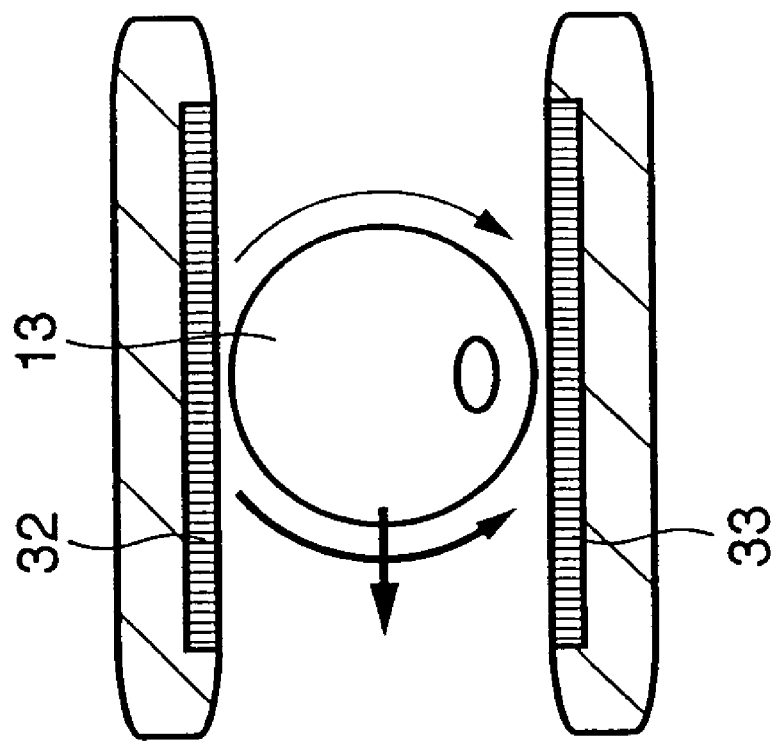
F I G. 12A
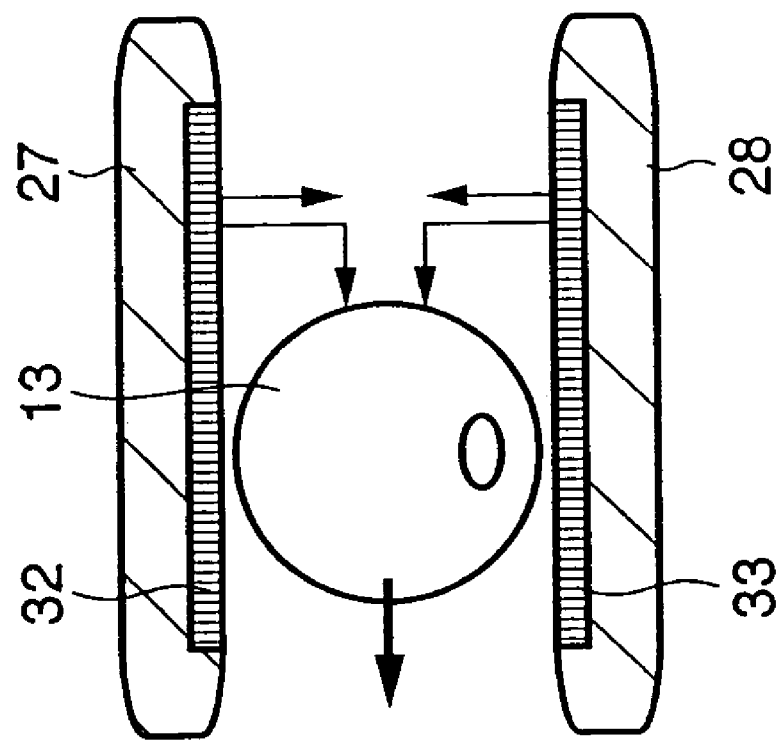
F I G. 12B

MANIPULATOR

FIELD OF THE INVENTION

The present invention relates to a manipulator which manipulates a target object and, more particularly, to a manipulator which grasps and moves a target object such as a cell or minute metal product, or executes various operations for minute objects and assembles them while controlling their attitude.

BACKGROUND OF THE INVENTION

A conventional typical manipulator which manipulates a minute object has an arrangement as shown in FIG. 16 (Japanese Patent Laid-Open No. 6-90770). Reference numeral 100 denotes an inverted microscope having a movable specimen table 101. A manipulation target object such as a cell in a petri dish 102 and the distal ends of manipulators 103 and 104 are observed through the inverted microscope 100. The micromanipulators 103 and 104 made of glass or the like are attached to holders 105 and 106 with triaxial actuators, respectively. Of the two manipulators 103 and 104, the manipulator 103 is used to hold the target object. The manipulator 104 controls the attitude of the target object or executes operations such as enucleation or nucleus transplantation for it.

FIG. 17 is an enlarged view showing such cell manipulation. FIG. 17 shows a state in which the operation manipulator 104 is perforating a cell 107 having a cell nucleus 108 to enucleate the cell 107. The manipulators 103 and 104 are hollow glass capillaries. The distal end of the manipulator 103 is rounded to be suitable for grasp and not to damage the target object. The manipulator 104 has an appropriately sharpened distal end so that fine manipulation can be performed. For example, to enucleate the cell, the attitude of the cell 107 is controlled by rubbing and rotating it with the operation manipulator 104, as shown in FIG. 18A. Since the cell nucleus 108 is normally present at a one-sided position, the cell nucleus 108 is placed at the opposite position of the holding manipulator 103 (FIG. 18B). At this time, the suction force of the holding manipulator 103 is appropriately adjusted in synchronism with the movement of the operation manipulator 104. To release the cell 107, the pressure in the capillary of the holding manipulator 103 is changed to a positive pressure.

FIG. 19 shows another conventional manipulator (Japanese Patent Laid-Open No. 9-201783). Reference numeral 110 denotes a contact portion to a manipulation target object; and 109, a heater. Projecting and recessed portions 111 and 112 are formed in the contact surface to the target object to reduce the interaction force in grasping it. More specifically, the interaction force such as Van der Waals force or surface tension is reduced by decreasing the contact area to the target object. The heater 109 is arranged near the contact portion 110. The target object can be chucked/released by causing the heater 109 to generate heat to set, in the recessed portion 112, a pressure different from the peripheral pressure.

In the manipulators shown in FIGS. 16, 17, 18A and 18B, however, since the main body is made of glass, the flexibility is poor, and the degree of freedom at the working end is limited. For this reason, the workability in fine work is considerably poor. Such work is normally done under a microscope, and the visual field for it becomes narrow in inverse proportion to the magnification, resulting in difficulty in work. For example, when the attitude of the cell 107 is to be controlled, as shown in FIGS. 18A and 18B, the manipulator 104 can perform only a simple operation such as rubbing under remote control. For accurate and quick work, skills based on advanced training are necessary. In addition, the suction force of the holding manipulator 103 must appropriately be controlled in synchronism with rotation. During this work, the cell 107 often accidentally moves off its position. Furthermore, in a minute target object, the area force such as Van der Waals force or surface tension becomes large relative to the volume force such as gravity or inertial force. In this case, it may be impossible to release the target object that sticks to the manipulator.

The example shown in FIG. 19 takes a measure against this problem. However, the change in pressure is insufficient as a force. For a fine operation such as attitude control, the manipulator itself must largely move. Hence, the work is difficult in a narrow visual field. For the same reason, attitude control cannot be performed while keeping the target object firmly grasped. The influence of direct contact between the contact portion 110 and the target object is also sometimes nonnegligible.

SUMMARY OF THE INVENTION

The present invention has been made in consideration of the above situation, and has as its object to provide a manipulator having an arrangement which easily makes it possible to execute fine work such as attitude control while properly grasping even a minute target object.

In order to solve the above problems, according to the present invention, there is provided a manipulator comprising: a contact portion to a manipulation target object; a pressure chamber; fluid control means for controlling pressure in the pressure chamber; and an opening at the contact portion, the opening communicating with the pressure chamber, wherein the target object is manipulated by causing the fluid control means to control inflow/outflow of a fluid through the opening.

According to this manipulator, the target object is manipulated by causing the fluid control means to control inflow/outflow of the fluid through the opening. For this reason, fine work such as attitude control can easily be performed while properly grasping even a minute target object. The opening, pressure chamber, and fluid control means can have various relationships. For example, a plurality of opening sets each including at least one opening are prepared. The inflow/outflow of the fluid through the plurality of sets of openings can independently be controlled by the fluid control means. Each set of openings can communicate with at least one pressure chamber. Alternatively, each opening can communicate with a corresponding pressure chamber. To flexibly control the inflow/outflow of the fluid through the opening in accordance with the manipulation form of the target object, the sectional area of the opening is preferably much smaller than that of the pressure chamber.

On the basis of the above basic arrangement, the following detailed forms are available.

For example, the manipulator comprising a plurality of the openings for which the inflow/outflow of the fluid can independently be controlled by the fluid control means at the contact portion to the manipulation target object, wherein the fluid control means moves the target object in a desired direction by executing at least one of ejection of the fluid from the openings located on an opposite side of the direction in which the target object should be moved and drawing of the fluid from the openings located on the same side as the direction in which the target object should be moved (FIGS. 3A and 3B to be described later shows an example).

According to an embodiment of the present invention, the manipulator is a gripper type manipulator having a plurality of the contact portions at opposite positions and clamping the target object by the contact portions, and each of the contact portions has the opening for which the inflow/outflow of the fluid is controlled by the fluid control means (FIG. 10 to be described later shows an example).

According to an embodiment of the present invention, the contact portion has a recessed portion which is fitted on the target object to clamp the target object, and the contact portion having the recessed portion has the opening for which the inflow/outflow of the fluid is controlled by the fluid control means (FIG. 13 to be described later shows an example).

In such embodiments, it is preferred that the fluid control means controls attitude of the target object by generating a couple of forces by executing at least one of ejection and drawing of the fluid to a position shifted from a center of gravity of the target object (FIGS. 11A to 11C to be described later shows an example).

Further, it is preferred that the fluid control means performs an operation of feeding the target object by executing at least one of ejection of the fluid from the openings which are oppose each other on both sides and located on a side opposite to a direction in which the target object should be fed and drawing of the fluid from the openings which are oppose each other on both sides and located on the same side as the direction in which the target object should be fed (FIG. 12A to be described later shows an example).

Further, it is preferred that the fluid control means performs an operation of feeding the target object by controlling to make the fluid flowing through the openings on the same side as a direction in which the target object should be fed have a flow velocity different from that of the fluid flowing through the openings on a side opposite to the direction in which the target object should be fed (FIG. 12B to be described later shows an example).

According to an embodiment of the present invention, the pressure chamber is connected to a separated fluid storage and a feeding device.

In this case, the medium storage and the pressure chamber are partitioned by a channel valve so that a channel resistance against the movement of the fluid from the pressure chamber to the medium storage can be ensured (FIG. 9 to be described later shows an example).

The fluid control means preferably has temperature control means formed from, e.g., a resistance element or Peltier element facing the pressure chamber, or both of them. The temperature control means is preferably made of an element such as a piezoelectric element, a shape memory alloy, a photic driving element, or an electromagnetic driving element, which can externally control mechanical deformation, and deforms the pressure chamber (e.g., a microchamber) (FIGS. 8A to 8C to be described later shows an example).

The fluid control means and its driving circuit, the pressure chamber (e.g., a microchamber), and the opening may be integrally formed on a single material to form a module (FIG. 7 to be described later shows an example).

The fluid control means can be designed to be able to quickly eject and slowly draw, or slowly eject and quickly draw the fluid through the opening. The fluid is a medium such as a physiological saline solution, or a fat or fatty oil. When the manipulation target is a living organism such as a cell, the fluid is a physiological saline solution. When the manipulation target object is a metal component, the fluid is a fat or fatty oil.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

The accompanying drawings, which are incorporated in and constitute a part of the specification, illustrate embodiments of the invention and, together with the description, serve to explain the principles of the invention.

FIGS. 3A and 3B are views showing a minute object manipulating method using the manipulator according to the first embodiment;

FIGS. 4A to 4C are views showing an arrangement of a fluid control means according to the first embodiment;

FIGS. 5A to 5C are views showing another arrangement of the fluid control means according to the first embodiment;

FIGS. 11A to 11C are views for explaining a manipulating method in which the attitude of a target object is controlled by the manipulator according to the third embodiment;

FIGS. 12A and 12B are views for explaining manipulating methods in which a target object is fed by the manipulator according to the third embodiment;

DETAILED DESCRIPTION OF THE PREFERRED EMBODIMENTS

Preferred embodiments of the present invention will now be described in detail in accordance with the accompanying drawings.

First Embodiment

Figure 1:
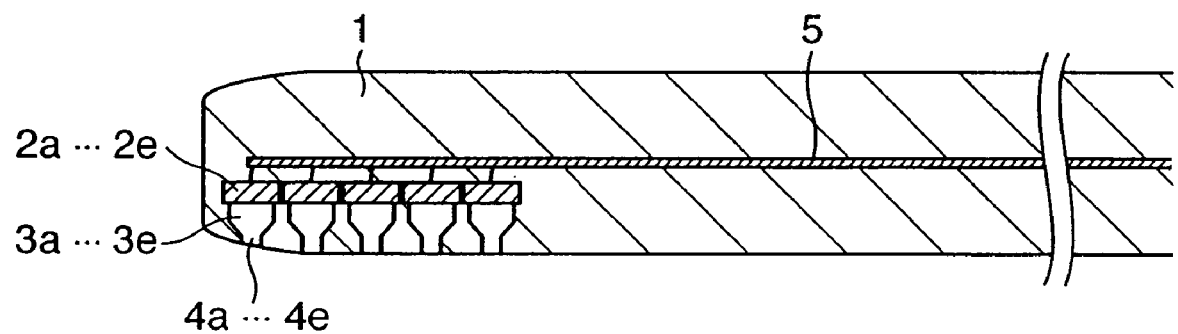
FIG. 1 is a sectional view showing a manipulator according to the first embodiment of the present invention.
Figure 2:
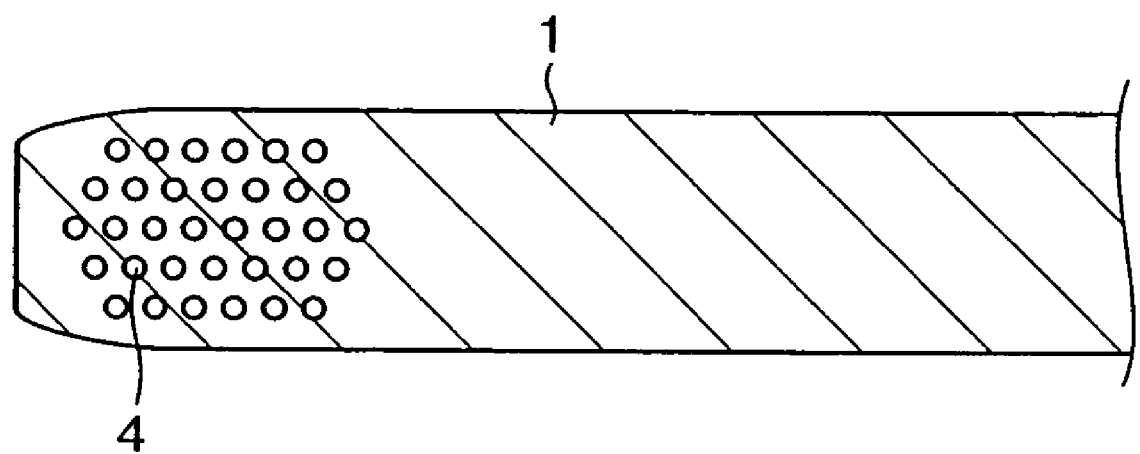
FIG. 2 is a front view showing the manipulator according to the first embodiment.

FIG. 1 is a sectional view of a manipulator according to the first embodiment of the present invention. Referring to FIG. 1, reference numeral 1 denotes a rod member made of a base material such as glass. Electrothermal transducers (heaters) $2a, \ldots, 2e$ can independently be energized through an electric wire by using a means such as a switch. In a steady state, pressure chambers (microchambers) $3a, \ldots, 3e$ are filled with the same liquid as the medium (e.g., a physiological saline solution) in which a target object such as a cell stands. During manipulation, the pressure chambers $3a, \ldots, 3e$ have an effect for increasing the pressure of the liquid which is thermally expanded by the heaters $2a, \ldots, 2e$ facing pressure chambers 3. Openings $4a, \ldots, 4e$ are connected to the pressure chambers $3a, \ldots, 3e$, respectively, and arranged at the contact portion to a manipulation target object. The target object is grasped, or its attitude is controlled as the fluid (medium) flows into or from the openings $4a, \ldots, 4e$. The sectional area of the opening 4 is set much smaller than that of the corresponding pressure chamber 3. In the sectional view of FIG. 1, the openings $4a, \ldots, 4e$ are illustrated one-dimensionally. Actually, they may be arranged two-dimensionally in an appropriate pattern in accordance with the target object or manipulation as shown in FIG. 2 (front view). In this case, heaters 2 and pressure chambers $3a, \ldots, 3e$ are also arranged in correspondence with the openings $4a, \ldots, 4e$. In the example shown in FIG. 2, the lines of the openings $4a, \ldots, 4e$ are laid out with a shift of a ½ pitch to increase an apparent resolution. The heaters $2a, \ldots 2e$ need not always be individually controlled. They may be divided into a plurality of groups, and the groups may individually be controlled. The method of dividing the heaters into groups to be individually controlled may be changeable. The reference numerals such as $2a, \ldots, 2e$ are used for the descriptive convenience and do not limit the numbers of components.

An example of the operation of the manipulator shown in FIG. 2 will be described. FIGS. 3A and 3B are views (the upper portion illustrates the upper surface, and the lower portion illustrates the section) for explaining an operation of moving a target object 13 gripped by the manipulator. Assume that the target object 13 such as a cell is grasped, as shown in FIG. 3A. When the target object is a minute object, a surface force such as a liquid crosslinking force is dominant as the grasping force. The suction force from the opening 4 may appropriately be used. To move the target object 13 from the right to the left in FIG. 13, the fluid is discharged from openings 11 and drawn from openings 12. The resultant force which acts on the target object 13 at this time feeds the target object 13 toward the distal end of the manipulator. Hence, the target object 13 can be fed to the distal end of the manipulator, as shown in FIG. 3B. More specifically, by controlling the fluid, the target object 13 can be moved by sliding or rolling it. When the openings for fluid control are sequentially switched, the target object can move over a relatively long distance. When the forms of electric supply to the heaters 2 are individually controlled, the flow rates at the openings 4 can individually be controlled. Hence, fine control can also be performed.

In the arrangement shown in FIG. 1, the next operation cannot be started unless the same pressure as the external pressure is set in the pressure chambers 3 after ejection or suction. In this case, the operation of manipulating the target object 13 is quickly executed, and the operation of returning the pressure is slowly executed by natural cooling or the like. The target object 13 can be manipulated only when the quick operation is performed.

The arrangement of the fluid control means 2 will be described next. FIGS. 4A to 4C show an example of the fluid control means. Reference numeral 14 denotes a switch; and 15, a DC power supply. When the switch 14 in the state shown in FIG. 4A is closed, as shown in FIG. 4B, the heater 2 is energized and generates heat. The internal pressure in the pressure chamber 3 increases due to thermal expansion of the medium in the pressure chamber 3. The medium is discharged from the opening 4 by a force corresponding to the degree of heat of the heater. After that, when the switch 14 is opened, as shown in FIG. 4C, the temperature in the pressure chamber 3 drops to decrease the internal pressure. Hence, the medium is drawn.

FIGS. 5A to 5C show a fluid control method using another principle in the same arrangement as that shown in FIGS. 4A to 4C. In this case, the heat value of the heater 2 is increased. The medium liquid is boiled by quick heating from the state shown in FIG. 5C to the state shown in FIG. 5B to generate a bubble 16. At this time, since the internal pressure in the pressure chamber 3 quickly rises, the medium is discharged outside. When energization is stopped, as in FIG. 4C, the pressure chamber 3 is cooled, and the medium is drawn. In this example, the fluid discharge force is large, as compared to the example shown in FIGS. 4A to 4C.

Figure 6:
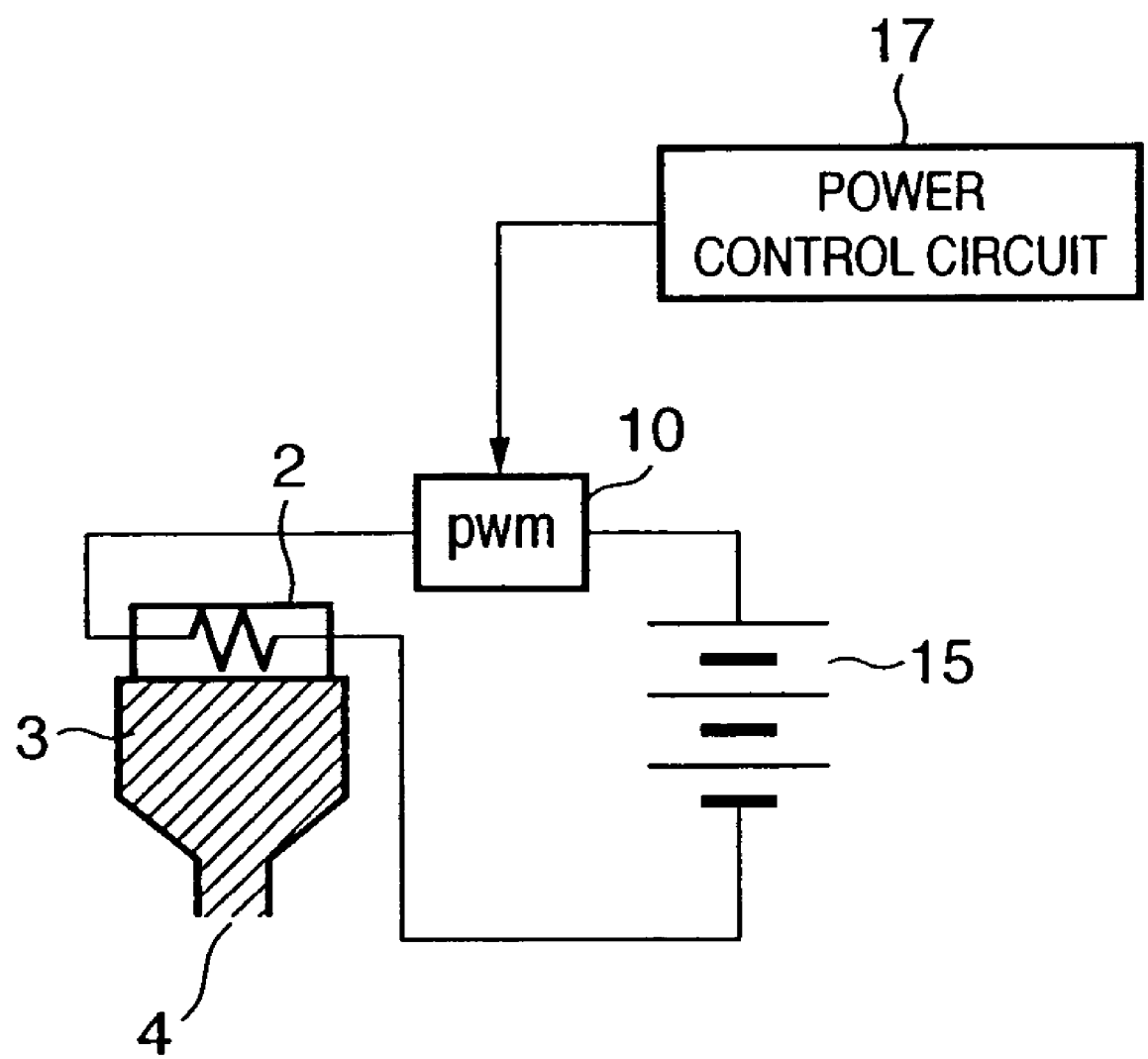
FIG. 6 is a view showing an arrangement of fluid control by the fluid control means according to the first embodiment.

In FIGS. 4A to 4C and 5A to 5C, the power is supplied/stopped by turning on/off the simple switch 14. The power to the heater 2 may be controlled by using a pwm circuit 10 and a power control circuit 17, as shown in FIG. 6. With this arrangement, the flow rate and flow velocity of the medium which passes through the opening 4 can be controlled more finely.

Figure 7:
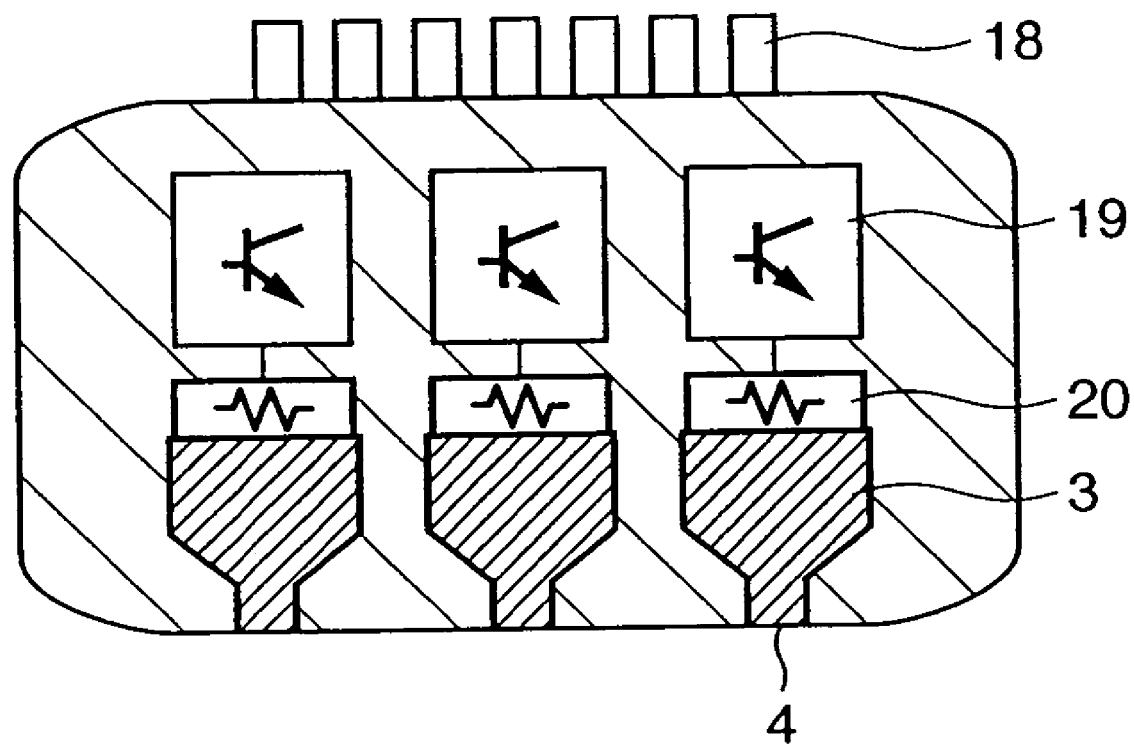
FIG. 7 is a view showing an arrangement in which the fluid control means according to the first embodiment is formed in a chip.

In the examples shown in FIGS. 4A to 4C, 5A to 5C, and 6, the heater 2 is used. Instead, a cooling element such as a Peltier element may be used. In this case, the operation upon energization is reversed to that shown in FIGS. 4A to 4C (the medium is drawn upon energization). A temperature control means 20 such as a heater or Peltier element, the pressure chamber 3, the opening 4, an electric circuit 19 such as a pwm circuit, and an electric terminal 18 may be formed on a single material by using a semiconductor material such as silicon, as shown in FIG. 7. When this module is fixed to the distal end of an arbitrary manipulator by adhesion or the like, an active manipulator can easily be formed.

Figure 8A:
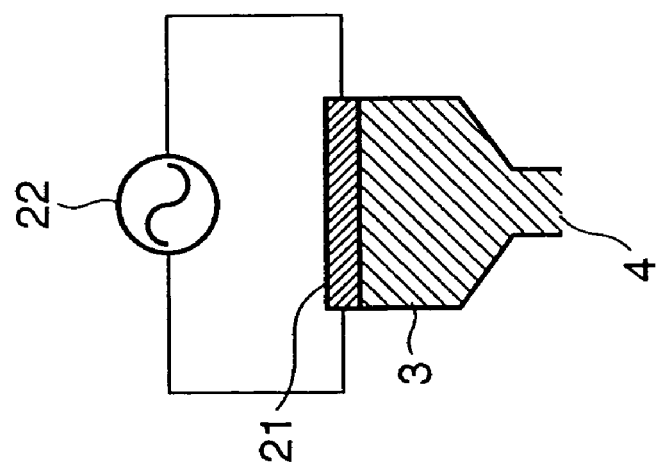
FIGS. 8A to 8C are views showing an arrangement in which the fluid control means according to the first embodiment uses mechanical deformation.
Figure 8B:
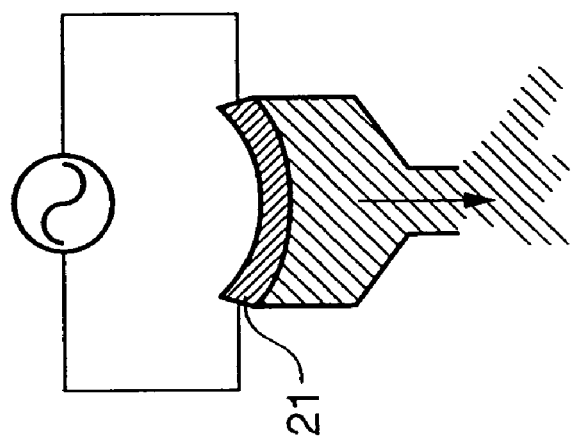
Figure 8C:
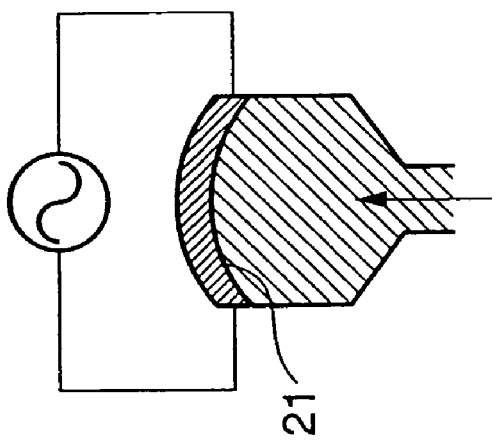

FIGS. 8A to 8C show another fluid control means according to the first embodiment. Reference numeral 21 denotes a piezoelectric element; and 22, a piezoelectric element driving power supply. The piezoelectric element 21 is integrated with the pressure chamber 3. When an electric field is applied, the piezoelectric element 21 is deformed to deform the pressure chamber 3. For example, when the piezoelectric element 21 bends from the state shown in FIG. 8A to the state shown in FIG. 8B, the fluid is discharged through the opening 4. When the piezoelectric element 21 bends as shown in FIG. 8C, the fluid can be drawn. As described above, the fluid can be controlled by changing the volume by deforming the pressure chamber 3. In the example shown in FIGS. 8A to 8C, the piezoelectric element 21 is arranged on the top plate. When the pressure chamber 3 can be deformed by the piezoelectric element 21 arranged on a side surface or the like, the same effect as described above can be obtained. As the driving source, the piezoelectric element 21 is used. Instead, any other element such as a shape memory alloy, an opto-mechanical deformation conversion element, or an actuator by an electromagnetic force can be used if it can control mechanical deformation of the pressure chamber 3.

In FIG. 1 described above, the openings 4 are formed in one end of a side surface of the manipulator. However, the opening formation position is not limited to this. Openings may be formed in the entire side surface. When the contact surface to the manipulation target object is at the distal end of the manipulator, the openings may be formed at the distal end. The openings 4 may be formed in two ends of the side surface. In the above example, a living organism such as a cell is handled. When a metal is handled as a target object, the fluid serving as the medium may be a fat or fatty oil. In place of a liquid, a gas may be used as the fluid (medium).

Second Embodiment

Figure 9:
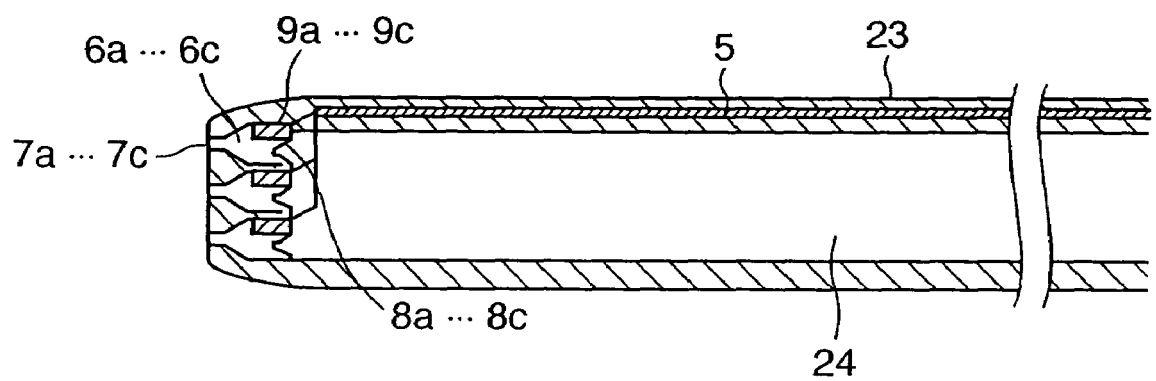
FIG. 9 is a sectional view showing a manipulator according to the second embodiment of the present invention.

FIG. 9 is a sectional view showing a manipulator according to the second embodiment. Reference numeral 23 denotes a rod member made of a base material such as glass. The rod member 23 has a hollow structure and is connected to a manipulation liquid reservoir (not shown). A hollow conduit 24 in the rod member 23 is filled with a manipulation liquid. Electrothermal transducers (heaters) $9a, \ldots, 9c$ can independently be energized through an electric wire 5. In a steady state, pressure chambers $6a, \ldots, 6c$ are filled with the liquid guided through the conduit 24. Inlet valves $8a, \ldots, 8c$ are formed between the pressure chambers $6a, \ldots, 6c$ and the conduit 24 to prevent backflow from the pressure chambers $6a, \ldots, 6c$ to the conduit 24. During manipulation, the inlet valves $8a, \ldots, 8c$ have an effect for increasing the pressure of the liquid which is thermally expanded by the heaters $9a, \ldots, 9c$. Openings $7a, \ldots, 7c$ are formed at the contact portion to a target object. The target object is grasped, or its attitude is controlled as the medium flows into or from the openings $7a, \ldots, 7c$. The reference numerals such as $6a, \ldots, 6c, 7a, \ldots, 7c, 8a, \ldots, 8c$, and $9a, \ldots, 9c$ are used for the descriptive convenience and do not limit the numbers of components. Actually, a set of a necessary number of openings or the like is prepared, as shown in FIG. 2.

In the second embodiment, the medium of the manipulation liquid can be different from the target object storage liquid, unlike the first embodiment. In the first embodiment, pressure transmission may be insufficient unless bubbles are removed from the openings by another means at the time of use. In the second embodiment, since the liquid can be injected from the manipulation liquid reservoir, bubbles in pressure chambers 6 can be removed. In addition, since even the pressure recovery operation in the pressure chambers 6 after the operation can be executed by supplying the manipulation liquid from the reservoir side, the operation speed can be increased.

In the arrangement shown in FIG. 9, openings 7 are formed in the distal end face. However, the present invention is not limited to this. The same effect as described above can also be obtained even when the openings are formed in a side surface of the rod member, as in the first embodiment. The heaters $9a, \ldots, 9c$ are arranged on the side surfaces of the pressure chambers 6 in FIG. 9. However, the present invention is not limited to this. The heaters can be arranged at any other positions as long as they can control the temperature of the pressure chambers $6a, \ldots, 6c$. When an appropriate feed pressure can be applied from the pressure chambers to the openings 7, the inlet valves $8a, \ldots, 8c$ may be omitted.

Third Embodiment

Figure 10:
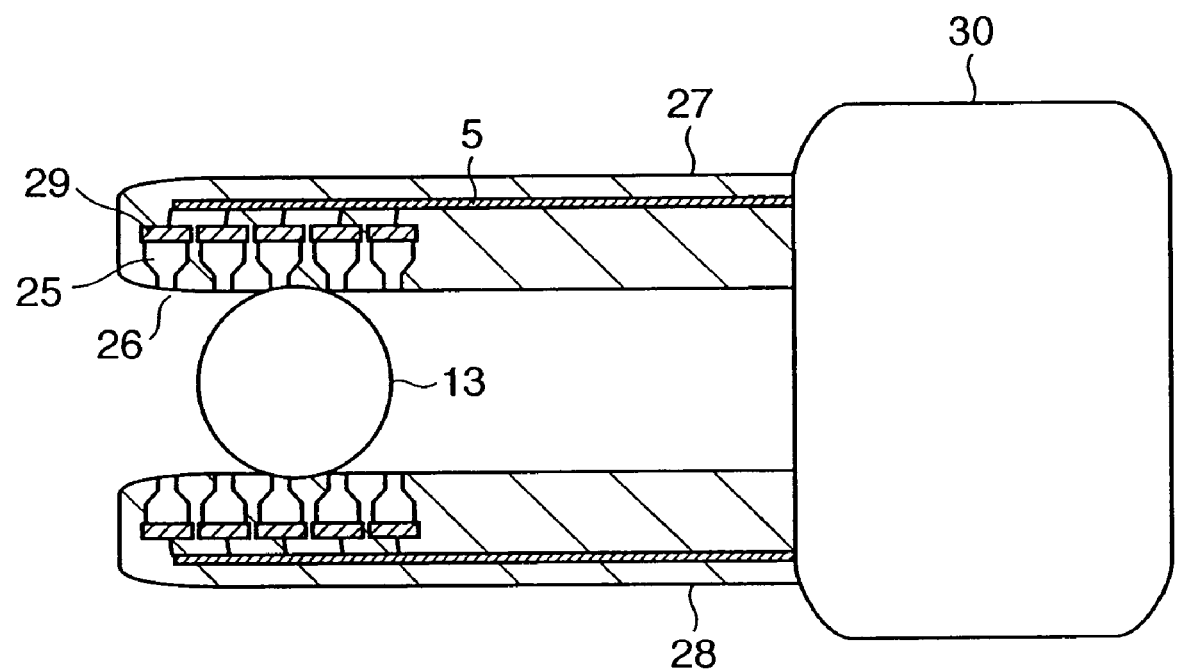
FIG. 10 is a sectional view showing a manipulator according to the third embodiment of the present invention.

FIG. 10 is a sectional view showing the arrangement of a manipulator according to the third embodiment. In this embodiment, two manipulators 27 and 28 which are the same as in the first embodiment are prepared to constitute a gripper structure. Each of the two manipulators 27 and 28 has a plurality of sets of temperature control means 29, pressure chambers 25, and openings 26 at the contact portion to a target object 13 such as a cell. These components can be controlled through an electric wire 5. An actuator 30 drives the manipulators 27 and 28. The manipulators 27 and 28 can be opened/closed in the vertical direction in FIG. 10 or relatively shifted in the horizontal direction in FIG. 10.

Figure 18A:
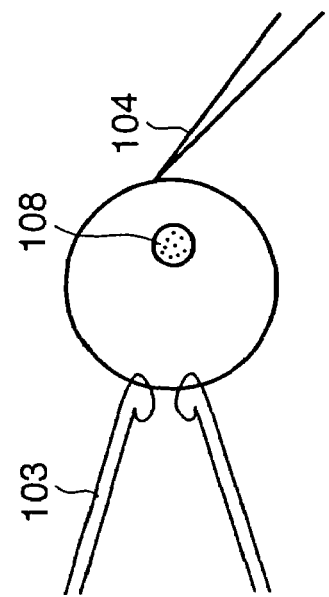
FIGS. 18A and 18B are views showing preparation for enucleation work in the conventional apparatus.
Figure 18B:
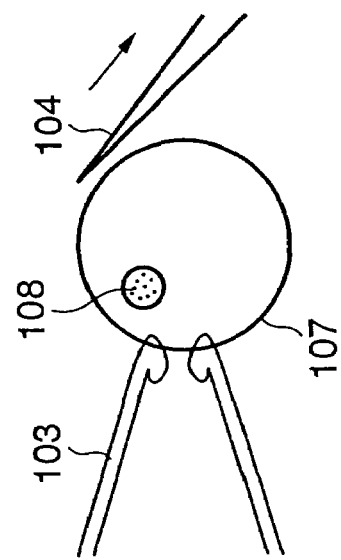
Figure 19:
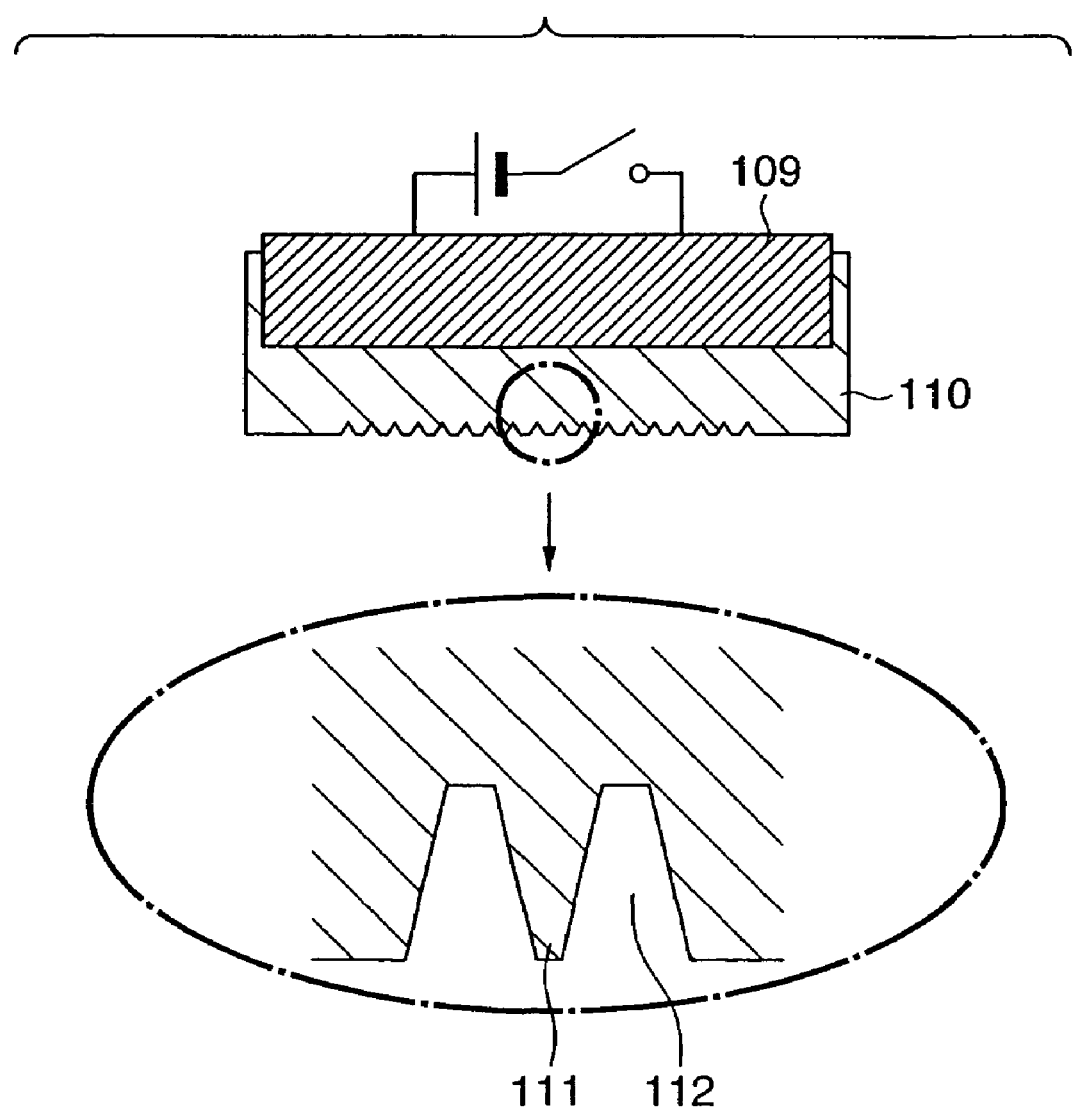
FIG. 19 is a view showing the contact portion of another conventional manipulator.

In this embodiment, especially, the attitude of the target object 13 can be controlled while it is kept firmly grasped. This operation will be described. In the conventional manipulator, such an operation is performed by rubbing the target object, as shown in FIGS. 18A and 18B. To do fine work such as attitude control, the contact area of the operation manipulator must be decreased. That is, the operation manipulator must have a sharp distal end. This structure readily damages the target object and requires delicate manipulation. In addition, the suction force of the suction pipette must be adjusted in synchronism with the movement of the operation manipulator. This work requires skills.

FIGS. 11A to 11C are explanatory views of the operation when the attitude of the target object 13 such as a cell is controlled by the gripper according to the third embodiment. Reference numerals 32 and 33 schematically represent manipulation portions (contact portions) having a plurality of sets of temperature control means, pressure chambers, and openings. Arrows in FIGS. 11A to 11C indicate movements of a fluid from the openings. The length of each arrow indicates the flow velocity. The manipulation portion 32 ejects the fluid to only the left side of the center of gravity of the target object 13 in FIGS. 11A to 1C. Conversely, the manipulation portion 33 ejects the fluid to only the right side of the center of gravity of the target object 13. With the above manipulation, a couple of forces are generated around the center of gravity of the target object 13 so that it rotates counterclockwise as shown in FIGS. 11A to 11C. When the fluid is ejected from openings separated from the center of gravity of the target object as far as possible, or the flow velocity is increased as the distance from the center of gravity increases, as shown in FIGS. 11A to 11C, a larger turning force can be obtained. Since a minute object has small inertia and does not overrun by coasting, it can relatively easily be positioned. In the example shown in FIGS. 11A to 11C, the fluid is ejected. Instead, the fluid may be drawn. In this case, the fluid is drawn from openings which are located on the opposite side of the ejecting openings and not used for ejection in FIGS. 11A to 11C.

When the attitude of the target object 13 is controlled by the above method, the risk to damage the target object can be reduced, as compared to the conventional method shown in FIGS. 18A and 18B, in which the target object is poked with the sharp manipulation needle. In addition, since the target object can be manipulated while it is kept firmly held by the two manipulators 27 and 28, more proper manipulation can be executed.

FIGS. 12A and 12B are views showing operation examples in which the grasped target object 13 is fed. Referring to FIG. 12A, the target object 13 is fed forward by ejecting the medium from openings which oppose each other behind the target object 13. This operation uses a fact that fluid components discharged from both sides collide to form a flow which pushes the target object 13 forward, as indicated by arrows. Referring to FIG. 12B, flows having different velocities are generated on the front and rear sides of the target object 13. In this case, the target object 13 is fed forward by generating a negative pressure on the front side by using a fact that the pressure decreases as the flow velocity increases due to the Bernoulli's theorem.

The manipulator according to this embodiment may be designed to supply a manipulation medium from a manipulation liquid reservoir, as in the second embodiment. In the third embodiment, when the two manipulators 27 and 28 are driven by the actuator 30, the same operation and combination as in the conventional manipulator are also possible. For example, the attitude of the target object is controlled by the fluid control means. Simultaneously, the target object is fed forward by fixing one manipulator, as in the conventional method, and using the translational motion of the other manipulator.

Fourth Embodiment

Figure 13:
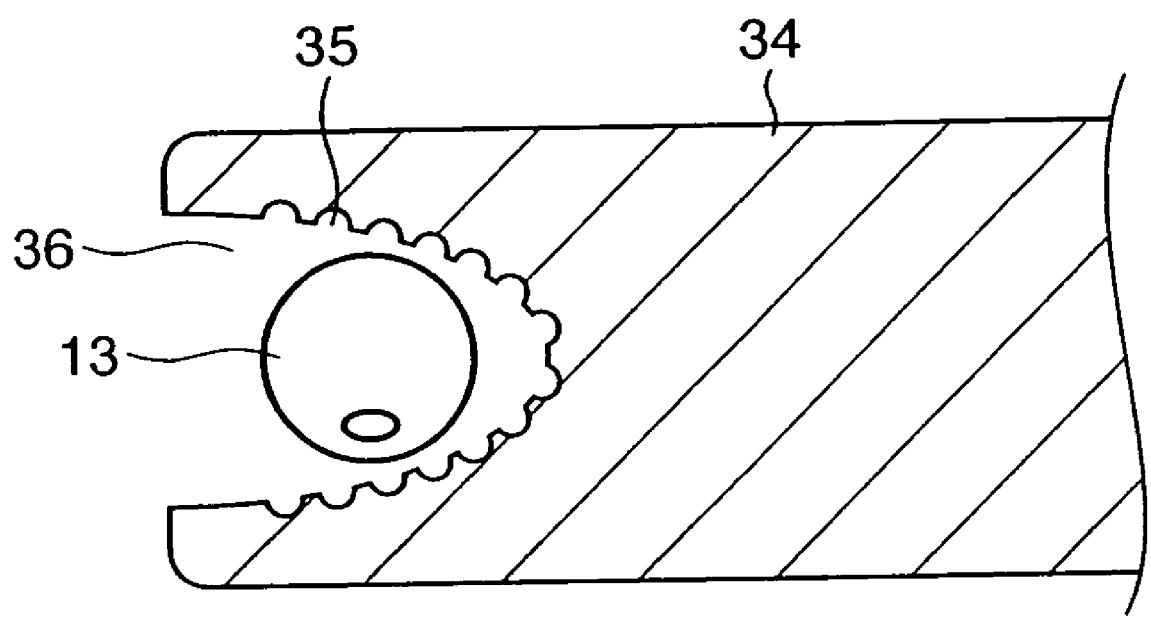
FIG. 13 is a sectional view showing a manipulator according to the fourth embodiment of the present invention.

FIG. 13 shows the distal end portion of a manipulator according to the fourth embodiment. Reference numeral 34 denotes a thin rod member made of, e.g., glass. The rod member 34 has, at its distal end, a grasping recessed portion 36 corresponding to the size of a target object 13. A plurality of sets 35 of fluid control means, pressure chambers, and openings are arrayed inside the recessed portion 36. The fluid control means can have the same structure as some examples described in the first embodiment.

As for manipulating method, attitude control or feed of the target object 13 can be executed by using the opposing sets 35 of fluid control means, pressure chambers, and openings, as in the third embodiment. A minute target object 13 can be grasped by fitting the target object in the recessed portion 36 by the force between the surfaces. When suction is appropriately performed by the sets 35 of fluid control means, pressure chambers, and openings, the target object can properly be grasped. In addition, a manipulation liquid reservoir may be prepared to supply a manipulation liquid, as in the second embodiment. As described above, as characteristic features of this embodiment, basic manipulation for grasping a minute object and controlling its attitude can be executed, and the arrangement is relatively simple.

Fifth Embodiment

Figure 14:
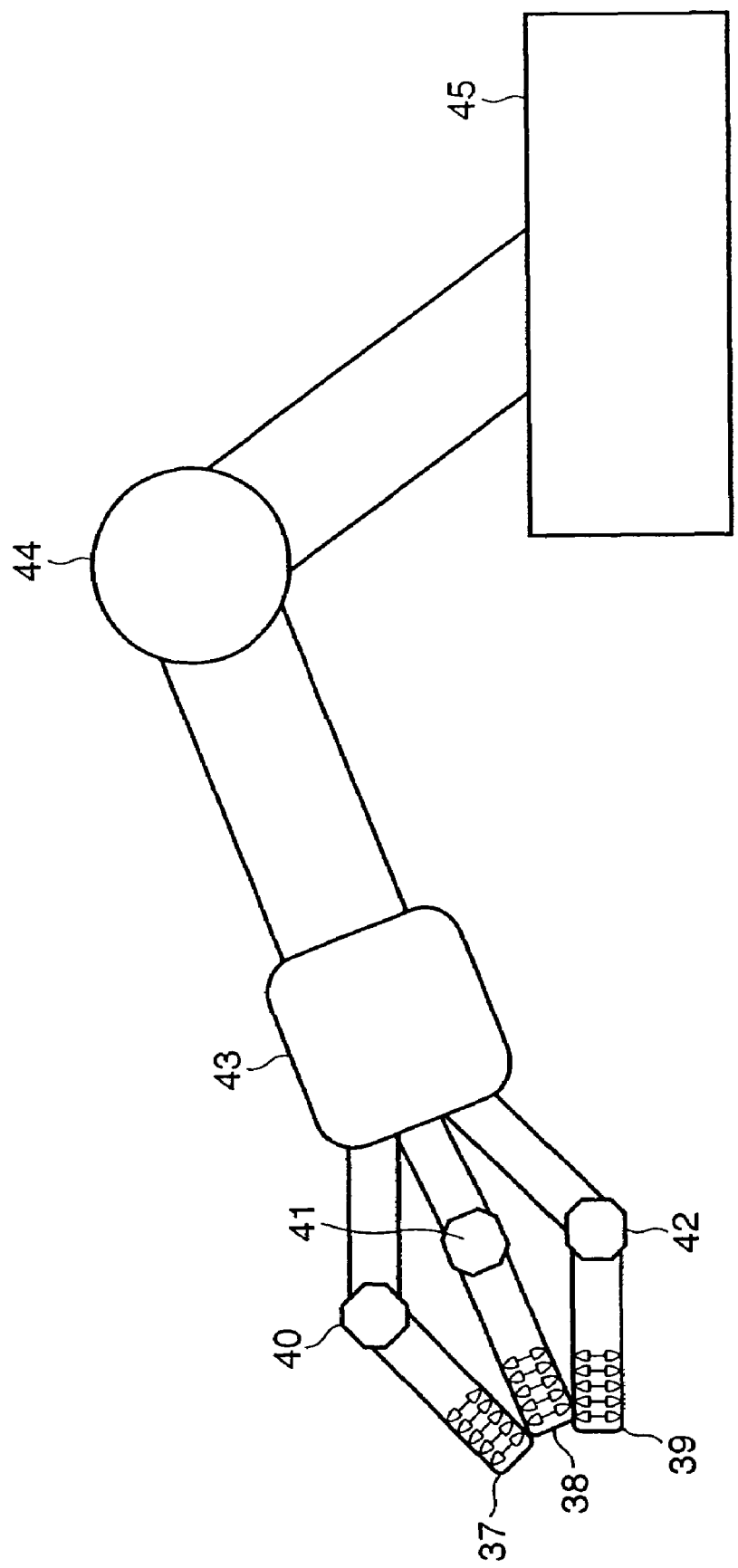
FIG. 14 is a view showing a robot arm with a hand according to the fifth embodiment of the present invention.

FIG. 14 shows a robot arm with a hand according to the fifth embodiment. Reference numerals 37, 38, and 39 denote manipulators of the first or second embodiment; 40, 41, 42, and 44 denote joints capable of bending; 43 denotes a rotary joint capable of rotation about the long axis of the arm; and 45 denotes a swivel base of the robot arm.

In the current mainstream of general assembly robots, an evacuator to suck a target object is prepared at the distal end portion of a robot arm having, e.g., the components 43 to 45. Such a robot performs an operation of grasping a component and assembling it to another position. However, this robot cannot substantially control the attitude of a component. Components must accurately be lined up on a palette or the like in advance. This requires an excess step and leads to an increase in cost. The robot arm with a hand according to this embodiment can grasp a component and simultaneously execute the same attitude control operation as in the manual operation by a worker. For this reason, the extra step of lining up components on a palette can be omitted.

Figure 15:
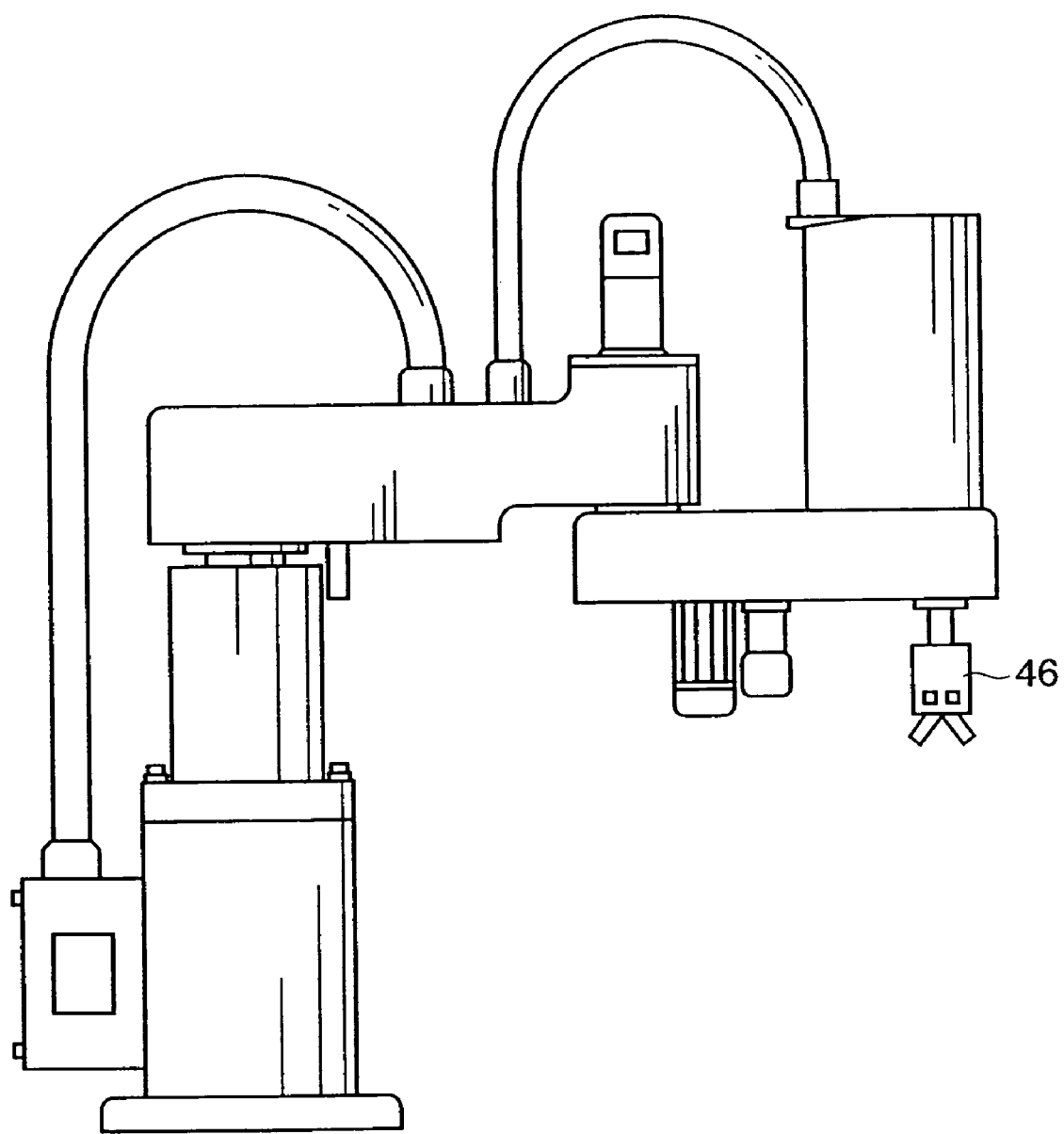
FIG. 15 is a view showing another arrangement of the robot hand according to the fifth embodiment.
Figure 16:
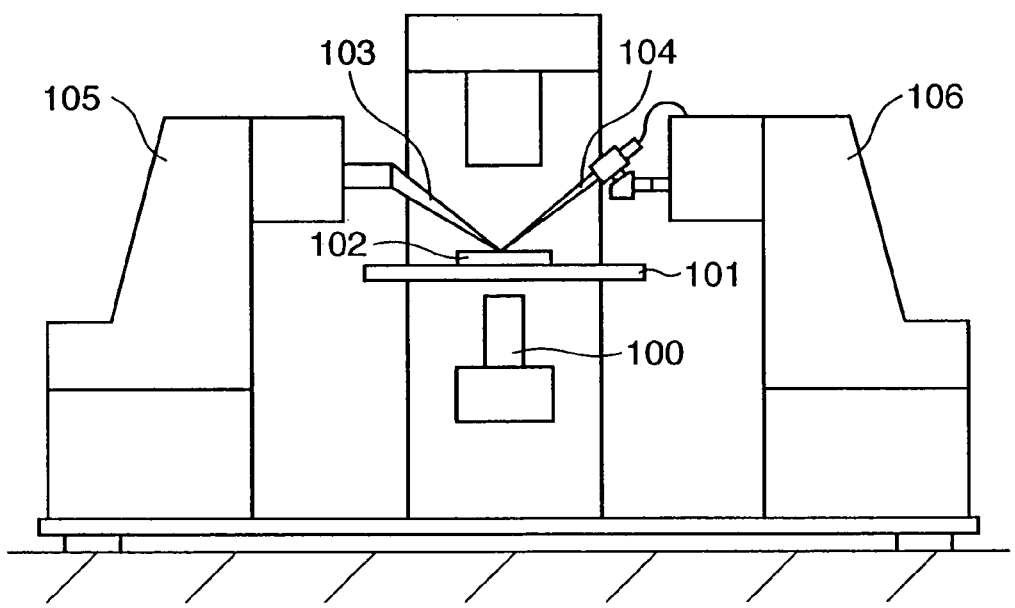
FIG. 16 is a view showing a conventional general micromanipulator apparatus.
Figure 17:
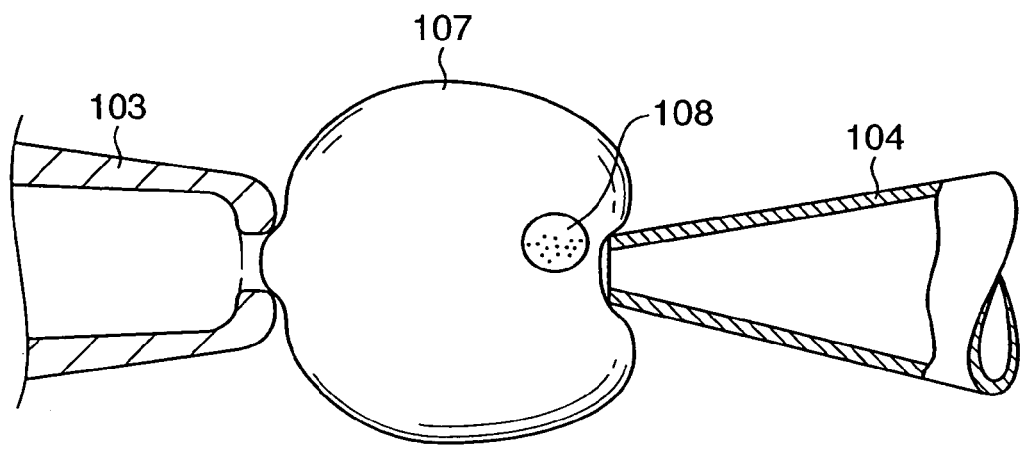
FIG. 17 is an enlarged view showing enucleation work in the conventional apparatus.

FIG. 14 illustrates three manipulators at the distal end. However, the number of manipulators is not limited to this, and at least one manipulator suffices. Normally, to cause a multi-fingered hand to firmly grasp a three-dimensional object, three fingers suffice. To cause the finger portion to perform the manual operation while firmly grasping the target object, it is said that the number of fingers must be four. In this embodiment, the manual operation can be performed while firmly grasping the target object with three fingers. The arm portion is not limited to the articulated robot as shown in FIG. 14. For example, a scalar structure as shown in FIG. 15, which is often used for pick & place, may be used. In this case, the manipulator of the present invention is used in a manipulator portion 46.

As has been described above, according to the manipulator of each of the preferred embodiments of the present invention, fine work such as attitude control can be executed while properly grasping not only a relatively large target object but also a minute target object.

As many apparently widely different embodiments of the present invention can be made without departing from the spirit and scope thereof, it is to be understood that the invention is not limited to the specific embodiments thereof except as defined in the appended claims.

What is claimed is:

1. A manipulator comprising:
    first and second contact portions opposing each other and facing a manipulation target object;
    first openings at said first contact portion,
    second openings at said second contact portion, and
    fluid control means for performing an operation of feeding the manipulation target object by ejecting a first fluid at a first flow velocity from at least one of the first and second openings at a front side of the manipulation target object in a feeding direction and ejecting a second fluid at a second flow velocity slower than the first flow velocity from at least one of the first and second openings at a rear side of the manipulation target object in the feeding direction.

2. A manipulator comprising:
    first and second contact portions opposing each other and facing a manipulation target object:
    first openings at said first contact portion,
    second openings at said second contact portion, and
    fluid control means for controlling an attitude of the manipulation target object by ejecting a fluid from at least one of the first openings and drawing a fluid from at least one of the second openings at a right side of a center of gravity of the manipulation target object and ejecting a fluid from at least one of the second openings and drawing a fluid from at least one of the first openings at a left side of the center of gravity of the manipulation target object so as to generate a couple force around the center of gravity of the manipulation target object.

* * * * *

UNITED STATES PATENT AND TRADEMARK OFFICE
CERTIFICATE OF CORRECTION

PATENT NO. : 7,338,102 B2
APPLICATION NO. : 10/812878
DATED : March 4, 2008
INVENTOR(S) : Tadash Hayashi It is certified that error appears in the above-identified patent and that said Letters Patent is hereby corrected as shown below:

Title Page

[56] REFERENCES CITED:

FOREIGN PATENT DOCUMENTS, "JP   61-95740   6/1985" should read --JP   61-95740   6/1986--.

COLUMN 8:

Line 37, "1C." should read --11C.--.

Signed and Sealed this

Twenty-fourth Day of March, 2009

JOHN DOLL
*Acting Director of the United States Patent and Trademark Office*